United States Patent [19]

Yamamoto

[11] Patent Number: 5,093,271
[45] Date of Patent: Mar. 3, 1992

[54] METHOD FOR THE QUANTITATIVE DETERMINATION OF ANTIGENS AND ANTIBODIES BY RATIO OF ABSORBANCES AT DIFFERENT WAVELENGTHS

[75] Inventor: Hideki Yamamoto, Mukou, Japan

[73] Assignee: Shimadzu Corporation, Japan

[21] Appl. No.: 124,997

[22] Filed: Nov. 24, 1987

[30] Foreign Application Priority Data

Nov. 28, 1986 [JP] Japan ................................ 61-284878
Jan. 7, 1987 [JP] Japan ................................ 62-1366
Jan. 7, 1987 [JP] Japan ................................ 62-1367

[51] Int. Cl.$^5$ ................ G01N 33/543; G01N 33/546
[52] U.S. Cl. .................................... 436/518; 435/7.1; 435/808; 436/513; 436/528; 436/531; 436/532; 436/533; 436/534; 356/320; 356/407
[58] Field of Search ............... 435/7, 174, 176, 177, 435/808, 513; 436/518, 528, 529, 531, 532–534, 193; 250/250; 422/68; 356/320, 407

[56] References Cited

U.S. PATENT DOCUMENTS

| | | | |
|---|---|---|---|
| 3,813,168 | 5/1974 | Honkawa | 356/97 |
| 4,136,959 | 1/1979 | Honkawa et al. | 356/418 |
| 4,180,327 | 12/1979 | Maeda et al. | 356/320 |
| 4,225,233 | 9/1980 | Ogan | 356/308 |
| 4,954,435 | 9/1990 | Krauth | 435/28 |

Primary Examiner—Sam Rosen
Assistant Examiner—Toni R. Scheiner
Attorney, Agent, or Firm—Bryan, Cave, McPheeters & McRoberts

[57] ABSTRACT

A method for the quantitative determination of antigen (or antibody) which comprises adding a sample containing an antigen (or antibody) to a dispersion of an insoluble carrier of fine particle size with an antibody (or antigen) fixed thereto to effect an antigen-antibody reaction, measuring absorbance of the reaction mixture, $A\lambda_1$ and $A\lambda_2$, at two different wavelengths, $\lambda_1$ and $\lambda_2$, and calculating the concentration of said antigen (or antibody) in the sample from the absorbance ratio $A\lambda_1/A\lambda_2$. This method is suitable for the measurment of the amount of an antigen or antibody in samples taken from living bodies using a simple procedure which has high sensitivity.

16 Claims, 7 Drawing Sheets

METHOD FOR THE QUANTITATIVE DETERMINATION OF ANTIGENS AND ANTIBODIES BY RATIO OF ABSORBANCES AT DIFFERENT WAVELENGTHS

BACKGROUND OF THE INVENTION

1. Field of the Invention

This invention relates to a method of the quantitative determination of antigens or antibodies. More specifically, it relates to a method for quantitative analysis for an antigen (or an antibody) which comprises allowing said antigen (or antibody) to react with an antibody (or antigen) supported on an insoluble carrier of fine particle size, irradiating light onto the resultant antigen-antibody complex, and measuring its absorbance at a specific wavelength; particularly a method that can measure the amount of an antigen or antibody in samples taken from living bodies simply and at a high sensitivity.

2. Description of the Prior Art

In the medical field, measuring the concentration of antigens or antibodies in samples taken from living bodies has recently been an important item for the diagnosis of diseases. Particularly, there has been a great demand for the development of a high-sensitivity method for quantitative analysis of those components which are present in samples (for example, the blood) in minute amounts, such as CRP (C-reactive protein) which is an acute reactive substance and AFP ($\alpha$-fetoprotein) which is a tumor marker.

The method conventionally used for the quantitative analysis of antigens and antibodies comprises dispersing latex particles of carrier supporting an antibody (or antigen) in a solvent, allowing an antigen (or antibody) to react with said particles, and measuring the increase in turbidity (or absorbance) of the dispersion caused by the antigen-antibody reaction at a wavelength in the range from 600 to 2400 nm, thereby determining the amount of said antigen (or antibody) (Japanese Examined Patent Publication No. 11575/1983).

Another method has been developed recently, which comprises supplying a dispersion containing agglutinated latex particles obtained from an antigen-antibody reaction to a sheath flow so as to make a flow of individual pieces of agglomerates, and analyzing the degree of agglutination by the light scattering method using a laser beam as light source, thereby determining the antigen (or antibody).

However, the above-mentioned methods have the following disadvantages.

In the former method, the change in absorbance due to latex agglutination is very small compared with the absorbance of the latex dispersion itself. If it is attempted to increase the change in absorbance by properly selecting the wavelength for measurement, the absorbance of the latex dispersion itself also tends to increase. Hence, the end-point assay (subtracting the absorbance of latex dispersion itself from the absorbance measured a sufficient period of time after the start of reaction) is difficult to adopt, and the two-point assay (measuring the change in absorbance at two-points over prescribed periods of time after the start of the antigen-antibody reaction) or rate assay (measuring the velocity of the change in absorbance), has to be employed. As a result, an automated analyzer must be used which automatically controls the operations from sample and reagent pipetting to absorbance measurement. In addition, the above-mentioned two-point assay requires a large quantity of costly latex reagent because a lower latex concentration results in lower agglutination speed and lower sensitivity.

Figure 13:
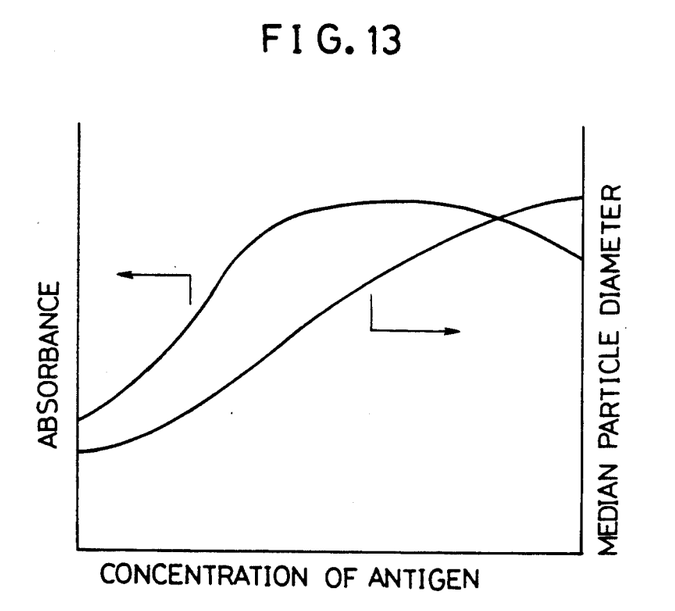
FIG. 13 shows graphs illustrating the relationship between the change in absorbance versus the change in median particle diameter caused by agglutination reaction in a model case.

Another problem associated with this method is that the change in absorbance is not determined by the degree of latex agglutination alone, because absorbance depends on both the number and size of the particles contained. As shown in FIG. 13, cases are known in which, although latex agglutination proceeds with increasing antigen concentration, absorbance begins to decline when the concentration reaches a certain level. Large errors are unavoidable in these cases.

These disadvantages have been eliminated in the latter method (the light scattering method); the result of measurement is dependent only upon the degree of latex agglutination, the end-point assay can be adopted, latex agglutination proceeds and sensitivty becomes higher with increasing reaction time, and sensitivty remains high even when the latex concentration is decreased. However, the problem is that an exclusive apparatus has to be used, because the flow channel must be of a sheath flow structure and a laser beam must be used as the light source to detect scattered light from individual particles.

This invention provides a simple method for measuring the concentration of an antigen (or an antibody) by a kind of end-point assay using a versatile spectrophotometer without having to employ any exclusive apparatus.

SUMMARY OF THE INVENTION

This invention relates to a method of the quantitative determination of an antigen (or an antibody) which comprises adding a sample containing said antigen (or an antibody) being tested to a dispersion of an insoluble carrier of fine particle size with an antibody (or an antigen) fixed thereto to effect an antigen-antibody reaction, measuring absorbance of the reaction mixture, $A\lambda_1$ and $A\lambda_2$ at two different wavelengths, $\lambda_1$ and $\lambda_2$, and calculating the concentration of said antigen (or antibody) in the sample from the absorbance ratio $A\lambda_1/A\lambda_2$.

This invention is based on the newly found fact that the absorbance ratio between two different wavelengths, $A\lambda_1/A\lambda_2$, is a function of the median diameter of particles suspended in the dispersion. The degree of increase in the median particle diameter due to agglutination of the insoluble carrier corresponds to the concentration of antigen (or antibody) in the sample; hence, the amount of antigen (or antibody) can be simply determined by the value of the absorbance ratio $A\lambda_1/A\lambda_2$.

Another merit of this method is that the end-point assay can be adopted, because this ratio scarcely affected by the small change of the particle concentration in the sample solution, and depends on the change of the relative particle size to the two wavelengths.

Thus, quantitative determination of an antigen (or an antibody) by utilizing the agglutination of insoluble carrier caused by an antigen-antibody reaction can be simply effected by the use of a versatile spectrophotometer, eliminating the need for an exclusive apparatus for automatic measurement of the velocity of absorbance changes or a special apparatus using a sheath flow and the laser-beam scattering technique.

In addition, high-sensitivity and low-cost quantitative analysis not expected with conventional methods can be achieved by properly selecting the combination of measuring wavelengths, $\lambda_1$ and $\lambda_2$, the particle size of the insoluble carrier, the particle concentration in the dispersion, reaction time and other factors (cell length, etc.).

DESCRIPTION OF THE PREFERRED EMBODIMENT

The antigens and antibodies that can be measured by the process of this invention include those which can exist in samples taken from living bodies. Illustrative examples include albumin, ferritin, AFP, $\beta_2$-microglobulin, mioglobin, CRP, ASO, RF, FDP, hCG, hPL, CEA, fibrinogen and gonadotropin (antigens), and immunoglobulins A, E, D, G and M, and $\gamma$-globulin globulin (antibodies).

The insoluble carriers of fine particle size used in the process of this invention are those materials which are insoluble in the dispersing medium employed and capable of fixing the antigens or antibodies. These include polystyrene, carobylated polystyrene, polymethylstyrenes, styrene-butadiene copolymers, carobylated styrene-butadiene copolymers, and poly(meth)acrylates. Preferred dispersing media are aqueous media, such as water, salt solutions and buffer solutions.

The antibody or antigen to be fixed to the insoluble carrier is selected so that an effective antigen-antibody reaction will take place with the antigen or antibody being measured. Fixation of this antibody or antigen to the insoluble carrier may be effected by any known methods: for example, adding the antibody or antigen to a dispersion of insoluble carrier, and stirring the mixture for a definite time to effect adsorption (so-called adsorption method); or adding the antibody (or antigen) and a coupling agent to a dispersion of an insoluble carrier bearing carboxyl groups, and stirring the mixture for a definite time to complete the fixation reaction (so-called covalent bonding method).

The particle diameter of insoluble carrier should preferably be in the range from 0.05 to 1.0 $\mu$m in terms of absorbance measurement range (usually 2 ABS or lower), and be in the range from 0.1 to 0.2 $\mu$m when high-sensitivity measurement is intended. Suitable concentration of the insoluble carrier in the dispersion is such that absorbance at 500 nm will be below 2 ABS, and should preferably be in the range from 1 to 100 mg/l for high-sensitivity measurement.

Such dispersions of carrier containing an antibody (or an antigen) fixed thereto as described above are commercially available, which may be advantageously used for the purpose of this invention.

Usually, the antigen-antibody reaction may be carried out by adding a test sample (for example, serum, plasma, lymphocytes and urine) to a dispersion of insoluble carrier as described above, and by stirring the mixture or allowing it to stand for a definite time. The suitable volume of test sample to be added is about 1/5 to 1/20 that of the dispersion. A reaction time of about 30 minutes usually suffices, but it should preferably be longer for high-sensitivity measurement; 0.5 to 2 hours when the concentration of insoluble carrier is in the range from 1 to 100 mg/l. Temperature has no appreciable effect upon the reaction, but is preferably in the range from 25° to 37° C. when considering that samples taken from living bodies are handled.

Higher sensitivity can be achieved when the two wavelengths used in the process of this invention are further apart from each other. However, since absorbance increases with decreasing wavelength and cannot be measured at low wavelengths, the optimum wavelengths should be selected depending upon the size and concentration of the particles and the concentration range of antigen (or antibody) to be measured. In actual practice, it is preferred that two wavelengths, $\lambda_1$ and $\lambda_2$, be selected within the visible and near infrared regions, usually within the range from 330 to 1000 nm. Within the range as defined above, the larger the difference between $\lambda_1$ and $\lambda_2$, the higher the sensitivity that will be achieved. For high-sensitivity measurement, in particular, a wavelength difference in the range from 300 to 600 nm is the most preferred.

Higher sensitivity is obtainable for a shorter cell length used for absorbance measurement, because a larger difference between two wavelengths can be adopted, but the length should preferably be in the range from 0.5 to 1 cm in terms of S/N ratio.

The concentration of antigen (or antibody) in a test sample can be determined from absorbance ratio $A\lambda_1/A\lambda_2$ (calculated from the values of absorbance measured at $\lambda_1$ and $\lambda_2$) using a calibration curve, which has previously been prepared using serial dilutions of an antigen (or antibody) solution of known concentration.

TEST AND EXAMPLES

Test

In this test were used six latices of different particle diameters as listed below (MISCELLANEOUS POLYSTYRENE SPHERES; products of Duke Scientific Corporation).

| Cat No. | Latex | Median Diameter Microns ($\mu m$) | Standard Deviation | Approx. Number per Package (5 ml) |
|---|---|---|---|---|
| 110 | Polystyrene spheres | 0.109 | .0027 $\mu m$ (2.5%) | $10^{13}$ |
| 111 | Polystyrene-butadiene spheres | 0.260 | .0022 $\mu m$ (0.9%) | $10^{12}$ |
| 113 | Polystyrene spheres | 0.500 | .0027 $\mu m$ (0.5%) | $10^{11}$ |
| 256 | Polystyrene spheres | 0.804 | .0048 $\mu m$ (0.6%) | $10^{11}$ |
| 114 | Polystyrene spheres | 1.09 | .008 $\mu m$ (0.7%) | $10^{10}$ |
| 115 | Polyvinyl-toluene spheres | 2.02 | .014 $\mu m$ (0.7%) | $10^{10}$ |

Figure 1:
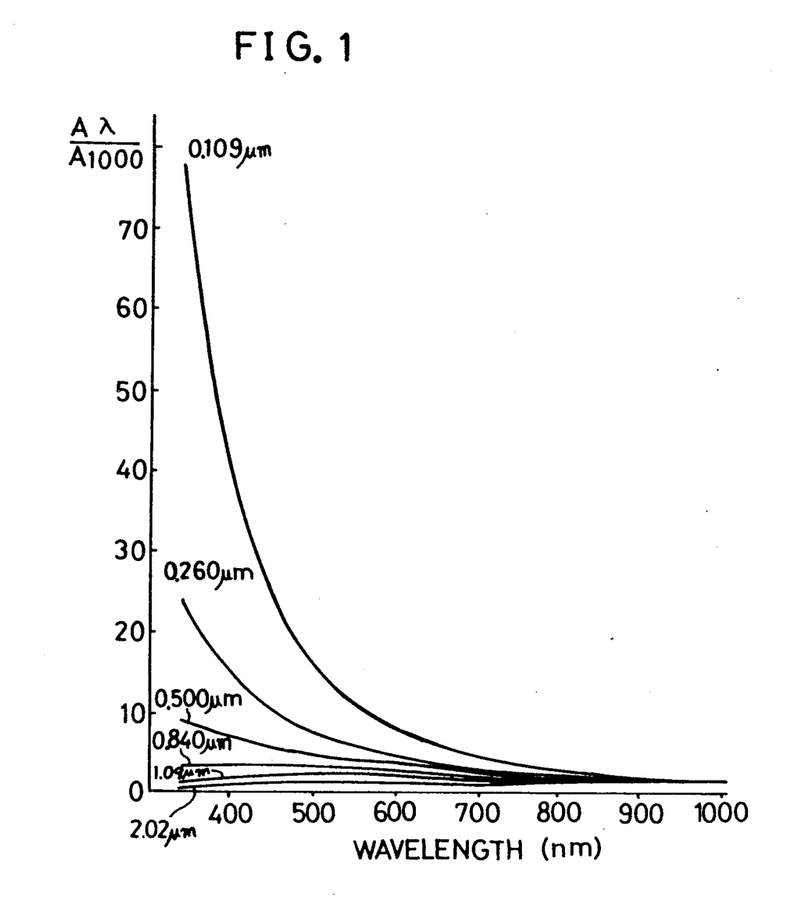
FIG. 1 is a graph illustrating the absorbance ratio at different wavelengths to that at 1000 nm measured with various latex dispersions being different in median diameter of the latex particle.

For each of the above six latices, five grades of dilutions with water were prepared (for Cat No. 110, preliminary dilution 1:21 followed by further dilution 1:1, 1:2, 1:3, 1:4 and 1:5; and for the other five latices, preliminary dilution 1:101 followed by further dilution 1:1, 1:2, 1:3, 1:4 and 1:5 ). Absorbance was measured for each of the dilutions thus prepared at different wavelengths in the range from 340 nm to 1000 nm, and the ratio of absorbance at varying wavelengths to that at 1000 nm ($A_\lambda/A_{1000}$) was calculated and plotted against wavelength. The result is shown in FIG. 1. Each of the values of $A_\lambda/A_{1000}$ shown in this figure is the average of values for five dilutions of different concentrations (n=5). Absorbance at each wavelength increased with increasing latex concentration, but the ratio $A_\lambda/A_{1000}$ remained practically constant. For example, the ratio $A_\lambda/A_{1000}$ for the latex of 0.260 $\mu m$ median particle diameter was 14.78-15.29, 7.22-7.63, 4.22-4.51, 2.78-2.97, 1.78-2.03 and 1.33-1.41 for $\lambda$=500, 600, 700, 800 and 900 nm, respectively. Further, the ratio $A_\lambda/A_{1000}$ for the latex of 0.804 $\mu m$ median particle diameter was 3.40-3.61, 2.88-3.08, 2.44-2.35, 1.88-1.93, 1.51-1.54 and 1.23-1.24, respectively.

Figure 2:
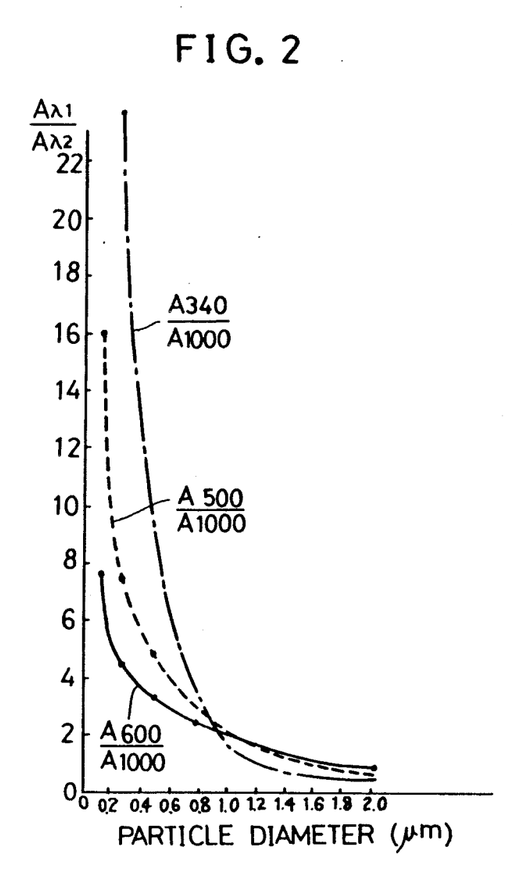
FIG. 2 shows the relation ship between $A_{340}/A_{1000}$, $A_{500}/A_{1000}$ and $A_{600}/A_{1000}$ versus latex particle diameter.

FIG. 2 shows the relationship between $A_{340}/A_{1000}$, $A_{500}/A_{1000}$ and $A_{600}/A_{1000}$ versus particle diameter based on the data shown in FIG. 1. It is apparent that the value of absorbance ratio decreases with increasing particle diameter in each case.

The result obtained in this test suggests that, in the agglutination reaction of carrier supporting an antibody (or an antigen), the degree of agglutination would increase with increasing concentration of antigen (or antibody) added, resulting in an increase in the median particle diameter and in a decline in the absorbance ratio $A_\lambda/A_{1000}$, and that the concentration of the antigen (or antibody) could be determined by this method.

It was also found that the smaller the particle diameter of latex supporting an antibody (or an antigen), the greater will be the change in the value of $A_\lambda/A_{1000}$ after agglutination. This means that the use of a latex of smaller particle diameter allows high-sensitivity measurement for samples of lower antigen (or antibody) concentration, and also broadens the concentration range of antigen (or antibody) measured because of the wider range of particle diameter in which its changes can be measured. In addition, it was also demonstrated that the larger the difference between the two wavelengths used for measurement, the greater the changes in absorbance ratio; that is, adoption of two wavelengths more apart from each other achieves high-sensitivity measurement for samples of lower antigen (or antibody) concentration.

EXAMPLE 1

A polystyrene latex (particle diameter: about 0.2 $\mu m$) with CRP antiserum fixed thereto (Cellatestam M, CRP latex reagent; product of Hitachi Chemical Co., Ltd.) was diluted 1:15 with a buffer solution (Cellatestam M, CRP diluent; product of Hitachi Chemical Co., Ltd.), 1500 $\mu l$ of this diluted dispersion was allowed to react with 12 $\mu l$ of standard serum containing a known amount of CRP at 37° C. for 90 minutes, and absorbance was measured at different wavelengths (cell-length:1 cm). Table 1 shows the data at 500, 600 700 and 1000 nm, and absorbance ratios, $A_{500}/A_{1000}$ and $A_{600}/A_{1000}$.

TABLE 1

| CRP Conc. (mg/dl) | $A_{500}$ | $A_{600}$ | $A_{700}$ | $A_{1000}$ | $A_{500}/A_{1000}$ | $A_{600}/A_{1000}$ |
|---|---|---|---|---|---|---|
| 0 | 1.308 | 0.764 | 0.480 | 0.163 | 8.02 | 4.69 |
| 0.2 | 1.346 | 0.798 | 0.507 | 0.171 | 7.87 | 4.67 |
| 0.4 | 1.446 | 0.881 | 0.571 | 0.207 | 6.99 | 4.26 |
| 0.6 | 1.481 | 0.934 | 0.622 | 0.229 | 6.20 | 3.91 |
| 0.8 | 1.560 | 1.014 | 0.693 | 0.282 | 5.53 | 3.60 |
| 1.0 | 1.580 | 1.065 | 0.752 | 0.330 | 4.79 | 3.23 |
| 2.0 | 1.469 | 1.058 | 0.806 | 0.441 | 3.33 | 2.40 |
| 5.0 | 1.411 | 1.077 | 0.806 | 0.464 | 3.04 | 2.23 |

Figure 3:
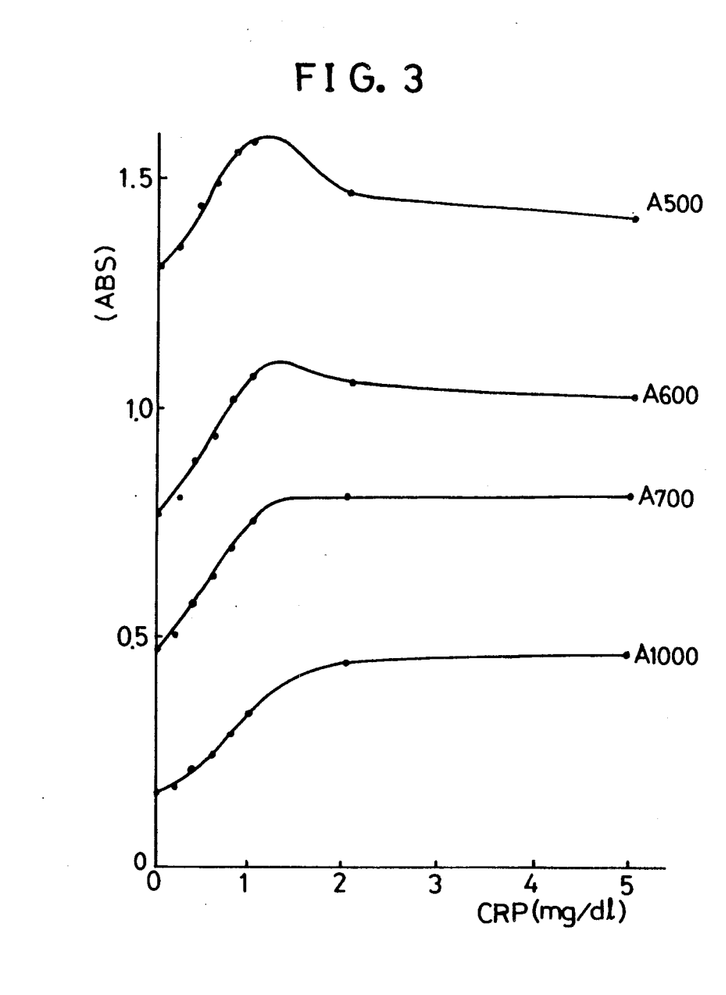
FIGS. 3, 4 and 5 show graphs illustrating the relationship between absorbance at various wavelengths, absorbance ratios ($A_{500}/A_{1000}$ and $A_{600}/A_{1000}$) and median particle diameter after latex agglutination reaction, versus CRP concentration, respectively.

FIG. 3 shows the relationship between absorbance at different wavelengths and CRP concentration (calibration curves in conventional method). In this figure, scatters in measured values due to scatters in the amounts of latices added are observed. In addition, the change in absorbance with CRP concentration is large for $A_{500}$, indicating a high sensitivity, but the value of absorbance reaches a maximum and begins to decline at a certain level of CRP concentration. No such reversion of curve is observed for $A_{1000}$, but the change in absorbance is small (low sensitivity) and the S/N ratio is also low at low concentrations (particularly 1 mg/dl or less).

Figure 4:
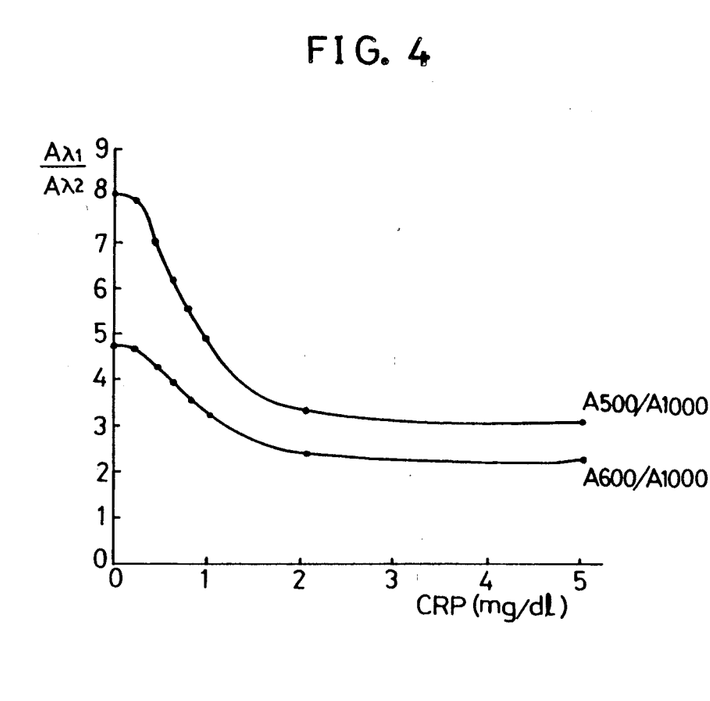

FIG. 4 shows calibration curves illustrating the relationship between absorbance ratios, $A_{500}/A_{1000}$ and $A_{600}/A_{1000}$, versus CRP concentration (typical cases of this invention). The change in absorbance ratio is large in low-concentration regions (high sensitivity) and any reversion of curve, as observed in FIG. 3, does not occur however high the CRP concentration may be. In addition, no scatter in measured value due to scatter in the amounts of latices added is observed in this case, because measurement of absorbance ratio at two different wavelengths offsets the scatter in each absorbance.

Figure 5:
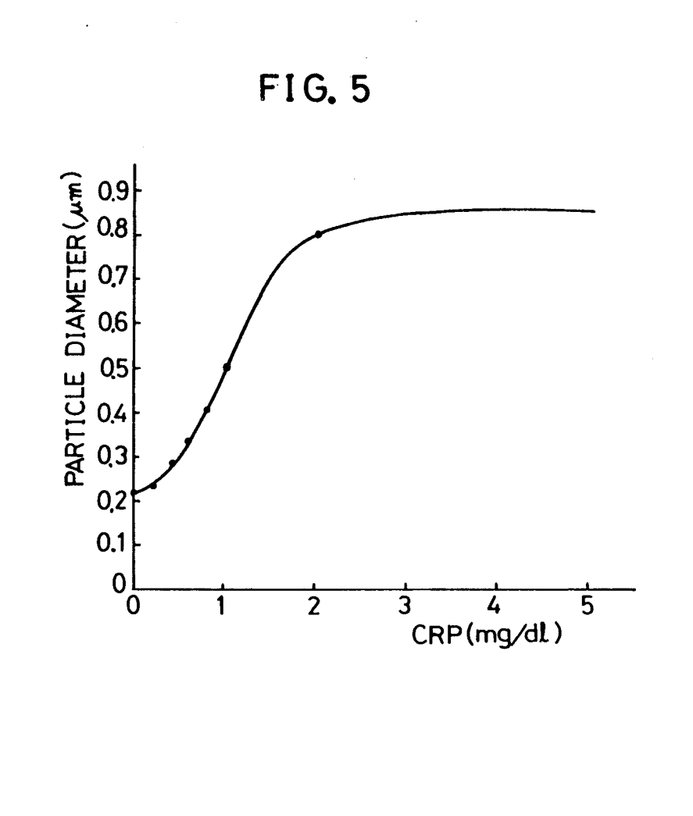

FIG. 5 shows the relationship between median diameter of antigen-antibody complex (agglutinated particles) obtained from the curve of FIG. 2 ($A_{600}/A_{1000}$) versus CRP concentration. This clearly indicates that the process of this invention provides a simple and useful method for quantitative determination of low-concentration antigens and antibodies based on latex agglutination.

EXAMPLE 2

The polystyrene latex with CRP antiserum fixed thereto used in Example 1 was diluted to different concentrations, each of the dilutions thus obtained was allowed to react with standard serum containing a known amount of CRP at 37° C. for 30 minutes and 90 minutes, and absorbance was measured at different wavelengths (cell-length : 1 cm). Table 2 shows the data at 340, 500, 600 and 1000 nm, and absorbance ratios, $A_{340}/A_{1000}$, $A_{500}/A_{1000}$ and $A_{600}/A_{1000}$.

low at high CRP concentrations because of the saturation of agglutination, while it remains rather high at low

TABLE 2

| Latex Dilution Ratio | CRP Conc. (mg/dl) | Reaction Time (min) | Absorbance | | | | Absorbance Ratio | | |
|---|---|---|---|---|---|---|---|---|---|
| | | | $A_{340}$ | $A_{500}$ | $A_{600}$ | $A_{1000}$ | $A_{340}/A_{1000}$ | $A_{500}/A_{1000}$ | $A_{600}/A_{1000}$ |
| 1/4 | 0 | 30 | 2.057 | 0.671 | 0.387 | 0.075 | 27.43 | 8.95 | 5.16 |
| | | 90 | 2.052 | 0.668 | 0.384 | 0.075 | 27.36 | 8.91 | 5.12 |
| | 0.2 | 30 | 2.035 | 0.687 | 0.401 | 0.081 | 25.12 | 8.48 | 4.95 |
| | | 90 | 2.047 | 0.716 | 0.424 | 0.092 | 22.25 | 7.78 | 4.61 |
| | 0.4 | 30 | 1.985 | 0.697 | 0.414 | 0.091 | 21.81 | 7.66 | 4.55 |
| | | 90 | 1.976 | 0.754 | 0.464 | 0.114 | 17.33 | 6.61 | 4.07 |
| | 0.6 | 30 | 2.128 | 0.791 | 0.478 | 0.111 | 19.17 | 7.13 | 4.31 |
| | | 90 | 2.084 | 0.867 | 0.553 | 0.152 | 13.71 | 5.70 | 3.64 |
| | 0.8 | 30 | 2.091 | 0.804 | 0.493 | 0.117 | 17.87 | 6.87 | 4.21 |
| | | 90 | 2.006 | 0.875 | 0.577 | 0.175 | 11.46 | 5.00 | 3.30 |
| | 1.0 | 30 | 2.158 | 0.868 | 0.542 | 0.139 | 15.53 | 6.24 | 3.90 |
| | | 90 | 2.025 | 0.918 | 0.619 | 0.203 | 9.98 | 4.52 | 3.05 |
| | 2.0 | 30 | 2.072 | 0.892 | 0.579 | 0.167 | 12.41 | 5.34 | 3.47 |
| | | 90 | 1.816 | 0.858 | 0.602 | 0.227 | 8.00 | 3.78 | 2.65 |
| | 5.0 | 30 | 2.175 | 0.966 | 0.635 | 0.191 | 11.39 | 5.06 | 3.32 |
| | | 90 | 1.831 | 0.828 | 0.626 | 0.254 | 7.21 | 3.47 | 2.46 |
| | 10.0 | 30 | 2.282 | 0.966 | 0.614 | 0.168 | 13.58 | 5.75 | 3.65 |
| | | 90 | 2.185 | 1.008 | 0.677 | 0.219 | 9.98 | 4.59 | 3.09 |
| 1/2 | 0 | 30 | | 1.310 | 0.766 | 0.160 | | 8.19 | 4.79 |
| | | 90 | | 1.308 | 0.764 | 0.163 | | 8.02 | 4.69 |
| | 0.2 | 30 | | 1.325 | 0.781 | 0.166 | | 7.98 | 4.70 |
| | | 90 | | 1.346 | 0.798 | 0.171 | | 7.87 | 4.67 |
| | 0.4 | 30 | | 1.394 | 0.833 | 0.185 | | 7.54 | 4.50 |
| | | 90 | | 1.446 | 0.881 | 0.207 | | 6.99 | 4.26 |
| | 0.6 | 30 | | 1.407 | 0.856 | 0.200 | | 7.04 | 4.28 |
| | | 90 | | 1.481 | 0.934 | 0.239 | | 6.20 | 3.91 |
| | 0.8 | 30 | | 1.477 | 0.913 | 0.223 | | 6.62 | 4.09 |
| | | 90 | | 1.560 | 1.014 | 0.282 | | 5.53 | 3.60 |
| | 1.0 | 30 | | 1.508 | 0.950 | 0.244 | | 6.18 | 3.89 |
| | | 90 | | 1.580 | 1.065 | 0.330 | | 4.79 | 3.23 |
| | 2.0 | 30 | | 1.596 | 1.080 | 0.339 | | 4.71 | 3.19 |
| | | 90 | | 1.469 | 1.058 | 0.441 | | 3.33 | 2.40 |
| | 5.0 | 30 | | 1.590 | 1.114 | 0.396 | | 4.02 | 2.81 |
| | | 90 | | 1.411 | 1.037 | 0.464 | | 3.04 | 2.23 |
| | 10.0 | 30 | | 1.580 | 1.161 | 0.412 | | 3.83 | 2.71 |
| | | 90 | | 1.358 | 0.986 | 0.415 | | 3.27 | 2.38 |
| 1/1 | 0 | 30 | | 1.923 | 1.140 | 0.239 | | 8.05 | 4.77 |
| | | 90 | | 1.913 | 1.132 | 0.238 | | 8.04 | 4.76 |
| | 0.2 | 30 | | 2.376 | 1.443 | 0.312 | | 7.61 | 4.63 |
| | | 90 | | 2.374 | 1.443 | 0.314 | | 7.56 | 4.60 |
| | 0.4 | 30 | | 2.436 | 1.498 | 0.333 | | 7.32 | 4.50 |
| | | 90 | | 2.447 | 1.514 | 0.341 | | 7.18 | 4.44 |
| | 0.6 | 30 | | 2.464 | 1.538 | 0.354 | | 6.96 | 4.34 |
| | | 90 | | 2.491 | 1.580 | 0.377 | | 6.61 | 4.19 |
| | 0.8 | 30 | | 2.483 | 1.572 | 0.374 | | 6.64 | 4.20 |
| | | 90 | | 2.528 | 1.649 | 0.417 | | 6.06 | 3.95 |
| | 1.0 | 30 | | 2.569 | 1.659 | 0.411 | | 6.25 | 4.04 |
| | | 90 | | 2.610 | 1.758 | 0.479 | | 5.45 | 3.67 |
| | 2.0 | 30 | | 2.588 | 1.813 | 0.554 | | 4.67 | 3.27 |
| | | 90 | | 2.505 | 1.840 | 0.729 | | 3.44 | 2.52 |
| | 5.0 | 30 | | 2.457 | 1.830 | 0.783 | | 3.14 | 2.34 |
| | | 90 | | 2.197 | 1.647 | 0.792 | | 2.77 | 2.08 |
| | 10.0 | 30 | | 2.387 | 1.795 | 0.818 | | 2.92 | 2.19 |
| | | 90 | | 1.956 | 1.469 | 0.703 | | 2.78 | 2.09 |

Figure 6:
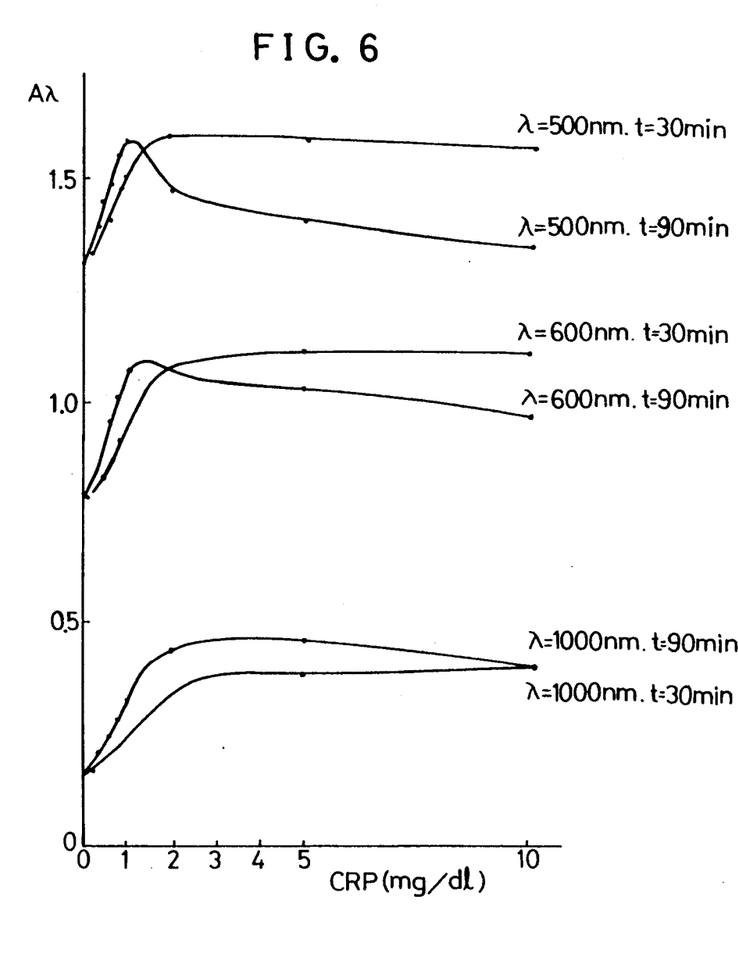
FIG. 6 shows a graph illustrating the effect of reaction time for the relationship between absorbance at various wavelengths versus CRP concentration.

FIG. 6 shows the relationship between CRP concentration and $A_\lambda$ at a dilution ratio of ¼ based on the data shown in Table 2 (curves for conventional method in which absorbance is measured only at one wavelength). It is clear from the figure that, at lower wavelengths, absorbance is excessively high and can hardly be measured in extreme cases, and reversion of curves as observed in FIG. 13 takes place.

Figure 7:
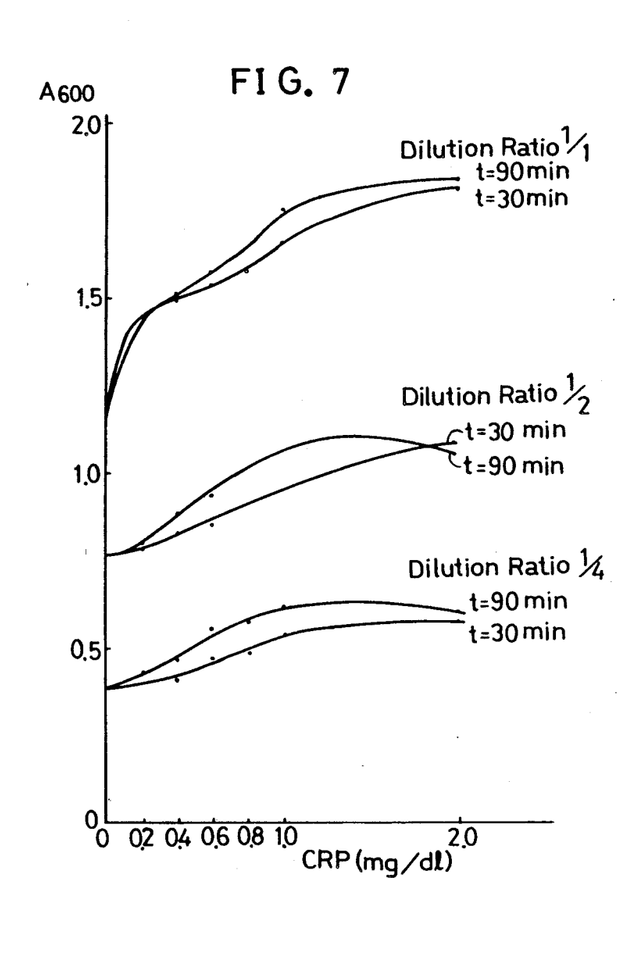
FIGS. 7, 8 and 9 show graphs illustrating the effect of the latex concentration at various reaction times for the relationship between absorbance, absorbance ratio and median particle diameter, respectively, versus CRP concentration.

FIG. 7 shows the relationship between CRP concentration versus absorbance at 600 nm ($A_{600}$) at different dilution ratios based on the data shown in Table 2. It is apparent from this figure that, when measuring the concentration of antigen (or antibody) from absorbance at one wavelength (conventional method), sensitivity becomes lower as latex concentration is decreased.

Figure 8:
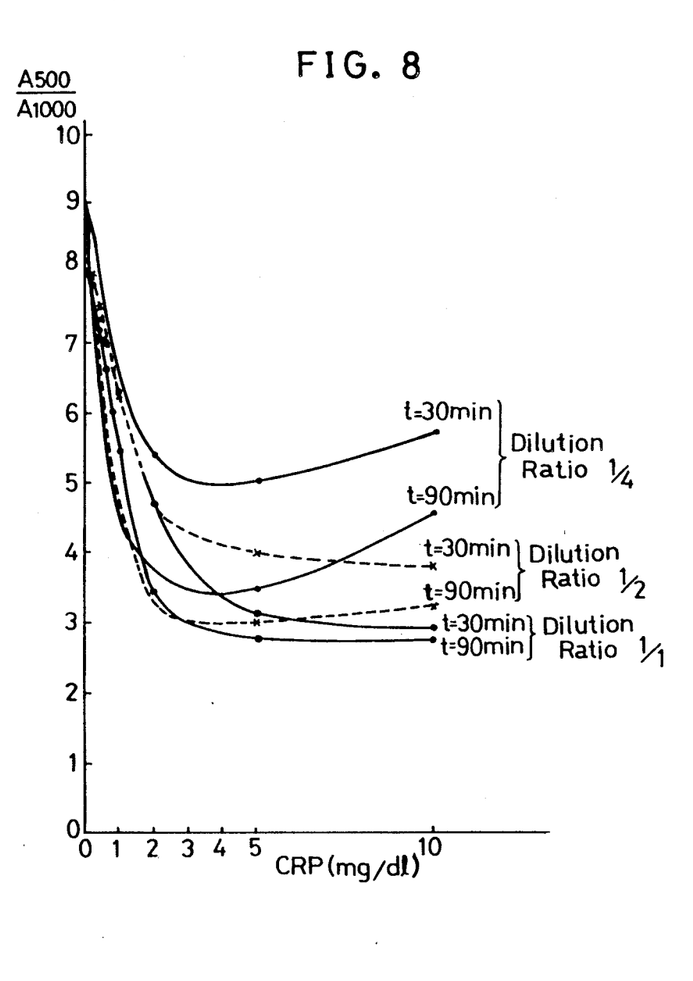
Figure 9:
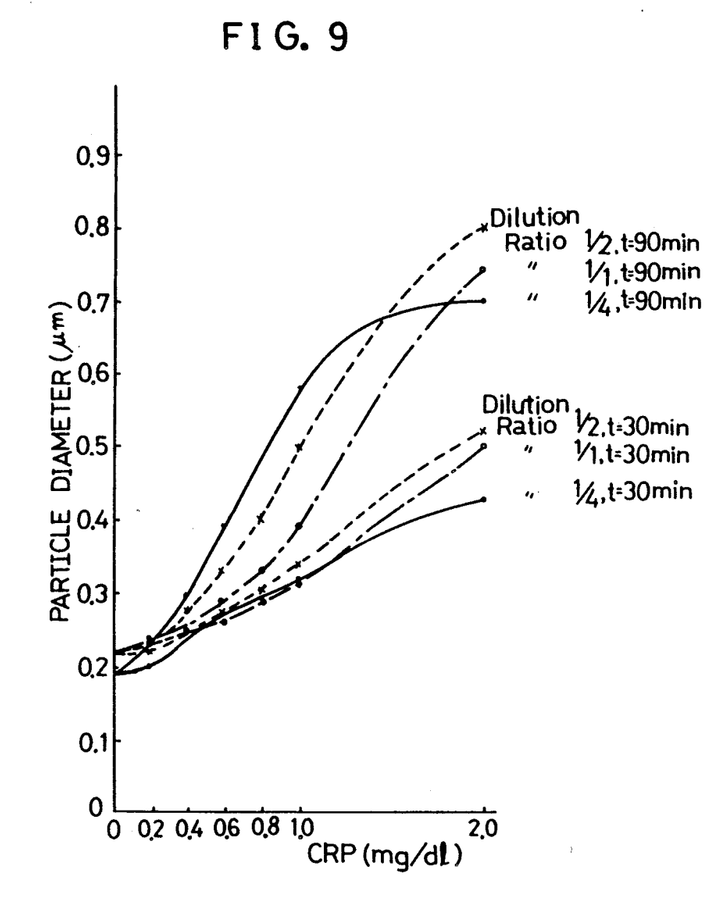

FIG. 8 shows the effect of the latex dilution ratio upon the relationship between CRP concentration and $A_{500}/A_{1000}$. As can be seen from the figure, sensitivity is CRP concentrations. This is because the change in median particle diameter increases with decreasing latex concentration as shown in FIG. 9. The median particle diameter in FIG. 9 was calculated from the values of $A_{600}/A_{1000}$ in Table 2 and the relationship shown in FIG. 2.

These indicate that adoption of a low latex concentration does not lead to any reduction in sensitivity, but achieves high sensitivity if a sufficient long time is taken for the reaction. This also makes for reduction in measurement cost because of the smaller amount of expensive latex reagent to be used.

Figure 10:
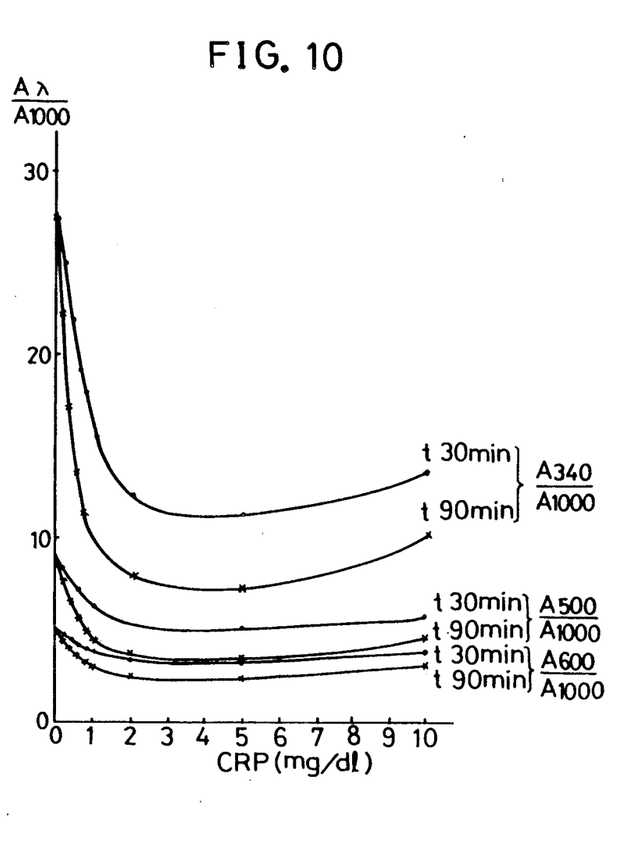
FIG. 10 show graphs illustrating the effect of the difference between two wavelengths for the relationship between absorbance ratio at various reaction times versus CRP concentration.

FIG. 10 shows the relationship between absorbance ratios, $A_{340}/A_{1000}$, $A_{500}/A_{1000}$ and $A_{600}/A_{1000}$, versus CRP concentration at a latex dilution ratio of ¼ based on the data shown in Table 2. It is apparent from this figure that higher sensivity can be achieved when the two wavelengths used, $\lambda_1$ and $\lambda_2$, are further apart from each other.

EXAMPLE 3

Figure 11:
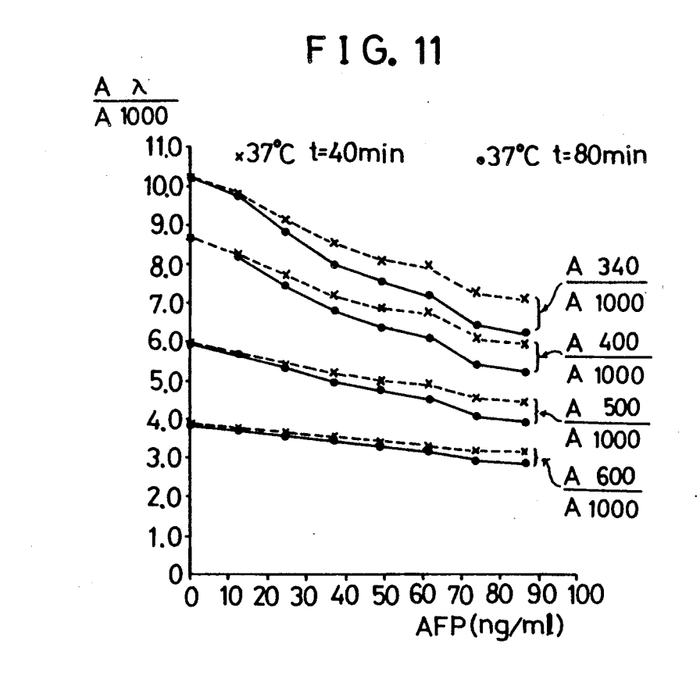
FIG. 11 shows graphs illustrating the relationship between concentration of AFP versus absorbance ratio between two different wavelengths at various reaction times.
Figure 12:
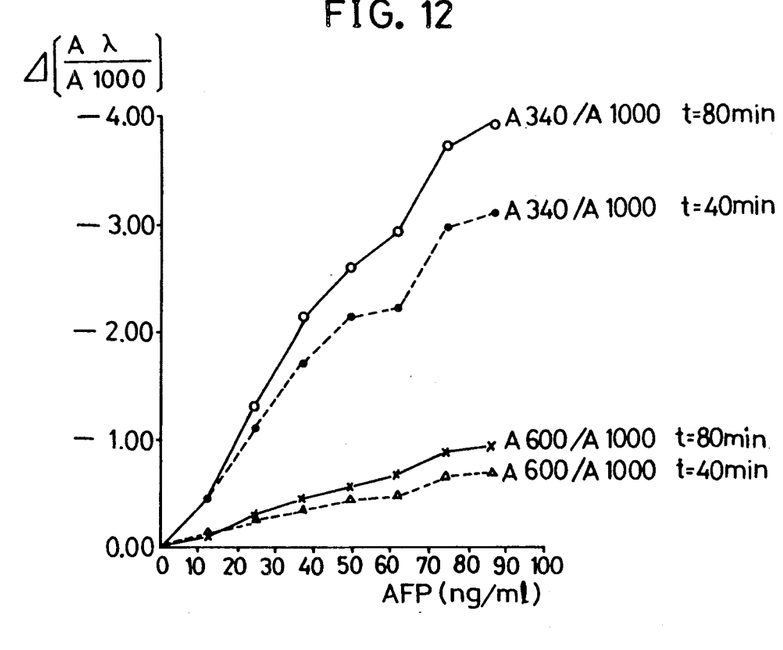
FIG. 12 illustrates the relationship between the changes in the absorbance ratio, as shown in FIG. 11, versus AFP concentration.

A polystyrene latex with anti-AFP antibody fixed thereto (anti-AFP antibody sensitized latex; product of IATRON LABORATORIES, INC.) was diluted 1:7 with its stabilizer solution (Product of IATRON), 1400 µl of this diluted dispersion was allowed to react with 50 µl of AFP solutions of different concentrations at 37° C. for 40 and 80 minutes, and absorbance was measure at 400, 500, 600 and 1000 nm ($A_{400}$, $A_{500}$, $A_{600}$ and $A_{1000}$) FIG. 11 shows the relationship between $A_\lambda/A_{1000}$ and AFP concentration, and FIG. 12 the relationship between the change in $A_\lambda/A_{1000}$ versus AFP concentration.

It was demonstrated that AFP can also be determined simply and at a high sensitivity based on absorbance ratio between two different wavelengths. Reproducibility of measured values was studied for values of the decrease in $A_{600}/A_{1000}$ The result obtained was $-0.26$ in mean value (corresponding to 26.9 ng/ml of AFP) and 0.03 in range (corresponding to 4.0 ng/ml of AFP), which indicates high reproducibility.

What we claimed is:

1. A method for determining the concentration of an antigen in a sample, comprising:
   (a) adding the sample to a test dispersion of a finely divided carrier having an antibody affixed thereto in a dispersing medium in which the carrier is insoluble, to produce an antigen-antibody reaction therebetween;
   (b) reacting the sample antigen with the carrier antibody for a predetermined reaction period;
   (c) measuring the absorbance (A) of the test dispersion after the reaction period at a first wavelength ($\lambda_1$) to determine a first absorbance value ($A\lambda_1$), and measuring the absorbance (A) of the test dispersion after the reaction period at a second wavelength ($\lambda_2$) to determine a second absorbance value $A\lambda_2$);
   (d) determining the absorbance ratio ($A\lambda_1/A\lambda_2$) of the first absorbance value ($A\lambda_1$) and the second absorbance value ($A\lambda_2$) of the test dispersion; and
   (e) determining the concentration of the sample antigen by comparing the absorbance ratio of the test dispersion ($A\lambda_1/A\lambda_2$) to reference absorbance ratios at said wavelengths of reference dispersions of said carrier having said antibody affixed thereto and reacted with pre-selected concentrations of said antigen.

2. The method as defined in claim 1, wherein the absorbance ratio of the test dispersion is comapred with the absorbance ratios of the reference dispersions in step (e) by:
   (1) measuring the reference absorbances of a plurality of the reference dispersions containing said preselected concentrations of said antigen after said reaction period at each of said wavelengths $\lambda_1$ and $\lambda_1$;
   (2) determining the reference absorbance ratios of the respective reference dispersions at said first and second wavelengths;
   (3) correlating said reference absorbance ratios to the concentrations of said antigen in said reference dispersions; and
   (4) comparing the absorbance ratio of the test dispersion with said correlated reference absorbance ratios to determine the concentration of antigen in the test dispersion.

3. The method as defined in claim 1, wherein the carrier has a median particle diameter of from 0.05 to 1.0 µm.

4. The method as defined in claim 1, wherein the carrier has a median particle diameter of from 0.1 to 0.2 µm.

5. The method as defined in claim 1, wherein the concentration of carrier in dispersing medium in step (a) is from 1 to 100 mg/l, and the predetermined reaction period of step (b) is from 0.5 to 2 hours.

6. The method as defined in claim 1, wherein the first wavelength ($\lambda_1$) of step (c) is from 330 nm to 1000 nm, and the second wavelength ($\lambda_2$) of step (c) is from 330 nm to 1000 nm.

7. The method as defined in claim 1, wherein the first wavelength ($\lambda_1$) and the second wavelength ($\lambda_2$) of step (c) have a difference in the range of from 300 nm to 600 nm.

8. The method as defined in claim 1, wherein the antigen in the sample is selected from the group consisting of albumin ferritin, alpha fetoprotein (AFP), $\beta_2$-mciroglobulin, mioglobin, C-reactive protein (CRP), anti-streptolysin-O (ASO), Rheumatoid Factor (RF), fibrin degradation products (FDP), human chronic gonadotropin (hCG), human placental lactogen (hPL), carcino-embryonil antigen (CEA), fibrinogen and gonadotropin.

9. A method for determining the concentration of an antibody in a sample, comprising:
   (a) adding the sample to a test dispersion of a finely divided carrier having an antigen affixed thereto in a dispersing medium in which the carrier is insoluble, to produce an antibody-antigen reaction therebetween;
   (b) reacting the sample antibody with the carrier antigen for a predetermined reaction period;
   (c) measuring the absorbance (A) of the test dispersion after the reaction period at a first wavelength ($\lambda_1$) to determine a first absorbance value ($A\lambda_1$), and measuring the absorbance (A) of the test dispersion after the reaction period at a second wavelength ($\lambda_2$) to determine a second absorbance value ($A\lambda_2$);
   (d) determining the absorbance ratio of the first absorbance value ($A\lambda_1$) and the second absorbance value ($A\lambda_2$) of the test dispersion; and
   (e) determining the concentration of the sample antibody by comparing the absorbance ratio of the test dispersion ($A\lambda_1/A\lambda_2$) to reference absorbance ratios at said wavelengths of reference dispersions of said carrier having said antigen affixed thereto and reacted with pre-selected concentrations of said antibody.

10. The method as defined in claim 1, wherein the absorbance ratio of the test dispersion is compared with the absorbance ratios of the reference dispersion in step (e) by:
    (1) measuring the reference absorbances of a plurality of the reference dispersions containing said preselected concentrations of said antigen after said reaction period at each of said wavelengths $\lambda_1$ and $\lambda_1$;

(2) determining the reference absorbance ratios of the respective reference dispersions at said first and second wavelengths;

(3) correlating said reference absorbance ratios to the concentrations of said antigen in said reference dispersions; and (4) comparing the absorbance ratio of the test dispersion with said correlated reference absorbance ratios to determine the concentration of antigen in the test dispersion.

11. The method as defined in claim 9, wherein the carrier has a median particle diameter of from 0.05 to 1.0 µm.

12. The method as defined in claim 9, wherein the carrier has a median particle diameter of from 0.1 to 0.2 µm.

13. The method as defined in claim 9, wherein the concentration of carrier in dispersing medium in step (a) is from 1 to 100 mg/l, and the predetermined reaction period of step (b) is from 0.5 to 2 hours.

14. The method as defined in claim 9, wherein the first wavelength ($\lambda_1$) of step (c) is from 330 nm to 1000 nm, and the second wavelength ($\lambda_2$) of step (c) is from 330 nm to 1000 nm.

15. The method as defined in claim 9, wherein the first wavelength ($\lambda_1$) and the second wavelength ($\lambda_2$) of step (c) have a difference in the range of from 300 nm to 600 nm.

16. The method as defined in claim 9, wherein the antibody in the sample is selected from the group consisting of immunoglobulin A, immunoglobulin E, immunoglobulin D, immunoglobulin G, immunoglobulin M and γ-globulin.

* * * * *

UNITED STATES PATENT AND TRADEMARK OFFICE
CERTIFICATE OF CORRECTION

PATENT NO. : 5,093,271

DATED : March 3, 1992

INVENTOR(S): HIDEKI YAMAMOTO

It is certified that error appears in the above-identified patent and that said Letters Patent is hereby corrected as shown below:

Column 1, line 17: Delete ";" and insert "," after "wavelength"."

Column 2, line 54: Insert --is-- after "ratio".

Column 2, line 17: Delete "sensitivty" and insert --sensitivity--.

Column 2, line 18: Delete "sensitivty" and insert --sensitivity--.

Column 3, line 11: Delete "relation ship" and insert --relationship--.

Column 3, line 51: Delete "globulin" before "glob-".

Column 6, line 14: After "600" insert --,--.

Column 9, line 12: Delete "measure" and insert -- measured--.

Column 9, line 22: Insert --.-- after "A $_{1000}$".

Column 9, line 42: Insert -- ( -- before "A$\lambda_2$)".

Column 9, line 55: Delete "comapred" and insert --compared --.

Column 9, line 62: After "and" delete "$\lambda_1$. and insert --$\lambda_2$--.

Column 9, line 20: "Reproducibility" should begin a new paragraph.

UNITED STATES PATENT AND TRADEMARK OFFICE
CERTIFICATE OF CORRECTION

PATENT NO. : 5,093,271
DATED : March 3, 1992
INVENTOR(S): HIDEKI YAMAMOTO

It is certified that error appears in the above-identified patent and that said Letters Patent is hereby corrected as shown below:

Column 10, line 26: Delete "mciroglobulin" and insert --microglobulin--.

Column 10, line 60: Delete "1" and insert --9--.

Column 10, line 62: Delete "dispersion" and insert --dispersions--.

Column 10, line 66: Delete "antigen" and insert --antibody--.

Column 10, line 68: After "and" delete "$\lambda_1$" and insert -- $\lambda_2$ --.

Column 11, line 5: Delete "antigen" and insert --antibody--.

Column 11, line 10: Delete "antigen" and insert --antibody--.

Signed and Sealed this

Twenty-third Day of November, 1993

BRUCE LEHMAN

Attesting Officer          Commissioner of Patents and Trademarks